United States Patent [19]

Hemzy et al.

[11] Patent Number: 5,314,662
[45] Date of Patent: May 24, 1994

[54] SAMPLE AUTOLOADER FOR USE WITH AN ANALYTICAL COMBUSTION FURNACE

[75] Inventors: Wayne R. Hemzy, St. Joseph; Thomas G. Knapp, Coloma, both of Mich.

[73] Assignee: Leco Corporation, St. Joseph, Mich.

[21] Appl. No.: 28,787

[22] Filed: Mar. 8, 1993

[51] Int. Cl.$^5$ .............. G01N 31/00; B65G 25/00; B66C 17/08

[52] U.S. Cl. .................. 422/62; 422/63; 422/65; 422/67; 422/78; 436/155; 414/176; 414/198; 414/940

[58] Field of Search .............. 422/62, 63, 65, 67, 422/78; 436/155; 414/158, 198, 176, 172, 940; 432/5, 6, 11, 152, 253

[56] References Cited

U.S. PATENT DOCUMENTS

| | | | |
|---|---|---|---|
| 3,489,521 | 1/1970 | Buckle et al. | 422/65 |
| 3,511,613 | 5/1970 | Jones | 422/63 |
| 3,578,412 | 5/1971 | Martin | 422/65 |
| 3,635,394 | 1/1972 | Natelson | 422/65 X |
| 4,049,134 | 9/1977 | Dolgen | 214/29 |
| 4,055,259 | 10/1977 | Sibrava | 214/17 A |
| 4,238,450 | 12/1980 | Bredeweg et al. | 422/63 |
| 4,701,096 | 10/1987 | Fisher, Jr. | 414/416 X |
| 4,752,219 | 6/1988 | Fisher, Jr. | 432/6 X |
| 4,770,590 | 9/1988 | Hugues et al. | 414/172 |
| 4,888,994 | 12/1989 | Nakamaki et al. | 414/161 X |
| 5,055,036 | 10/1991 | Asano et al. | 432/6 X |
| 5,064,617 | 11/1991 | O'Brien et al. | 422/78 |
| 5,246,667 | 9/1993 | Hemzy et al. | 422/80 |
| 5,256,060 | 10/1993 | Philipossian et al. | 432/6 X |

*Primary Examiner*—James C. Housel
*Assistant Examiner*—Milton I. Cano
*Attorney, Agent, or Firm*—Price, Heneveld, Cooper, DeWitt & Litton

[57] ABSTRACT

A sample autoloader loads a sample into a furnace and removes a sample from the furnace. The sample autoloader includes a sealing plate for sealing the furnace. The sample autoloader also includes a mechanism for pushing a sample into the furnace and removing a sample from the furnace. The sample autoloader may include a hotel which stores sample containers for automatic loading and a container which receives spent sample containers.

21 Claims, 11 Drawing Sheets

SAMPLE AUTOLOADER FOR USE WITH AN ANALYTICAL COMBUSTION FURNACE

BACKGROUND OF THE INVENTION

The present invention relates to sample loaders and, more particularly, to an automatic sample loader for a horizontal analytical furnace.

Horizontal analytic furnaces are well known. An example of such a furnace is disclosed in U.S. Pat. No. 5,064,617 entitled COMBUSTION SYSTEM issued to O'Brien et al. on Nov. 12, 1991. These furnaces are typically manually loaded with a sample. However, manual loading is time consuming and uncomfortable for the loader due to the high temperature within the combustion furnace and the high temperature of sample containers which are removed from the furnace.

Automatic sample loaders are known which mechanically load samples into an analytical combustion furnace. However, such loaders do not adequately seal the furnace following introduction of a sample. Accordingly, atmospheric contaminants such as nitrogen enter into the furnace and detrimentally effect the results of the analysis performed using analytical furnace. Additionally, these automatic loaders do not adequately provide for loading of sample containers and unloading hot spent containers.

SUMMARY OF THE INVENTION

The system of the present invention overcomes the difficulties encountered by the prior art. According to one aspect of the invention, an automatic loader seals the furnace following introduction of a sample into the furnace. Accordingly, the autoloader reduces the admission of contaminants into the furnace.

According to another aspect of the invention, the mechanism which pushes a sample container into the furnace hot zone is retracted to a cooler region of the furnace during combustion. The mechanism returns to the hot zone to retrieve the used boat after analysis is complete. Accordingly, the mechanism remains in the furnace after the furnace is sealed and until analysis is completed.

According to yet another aspect of the invention, an autoloader according to the invention delivers samples from a boat hotel to the furnace. The autoloader also removes the hot spent boats from the furnace and disposes them in a container where they can cool for further use or disposal.

The system according to the invention provides an efficient loader for moving samples into an analytical combustion furnace. Additionally, the autoloader provides a method of removing spent samples so that a new sample may be placed in the analytical furnace. Furthermore, the autoloader provides an automatic sealing mechanism which allows introduction of a sample into a furnace and subsequent sealing of the furnace to prevent the introduction of atmospheric contaminants to the analytical process.

These and other features, objects and advantages of the present invention will become apparent upon reading the following description thereof, together with reference to the accompanying drawings in which:

DETAILED DESCRIPTION OF THE PREFERRED EMBODIMENTS

Figure 1:
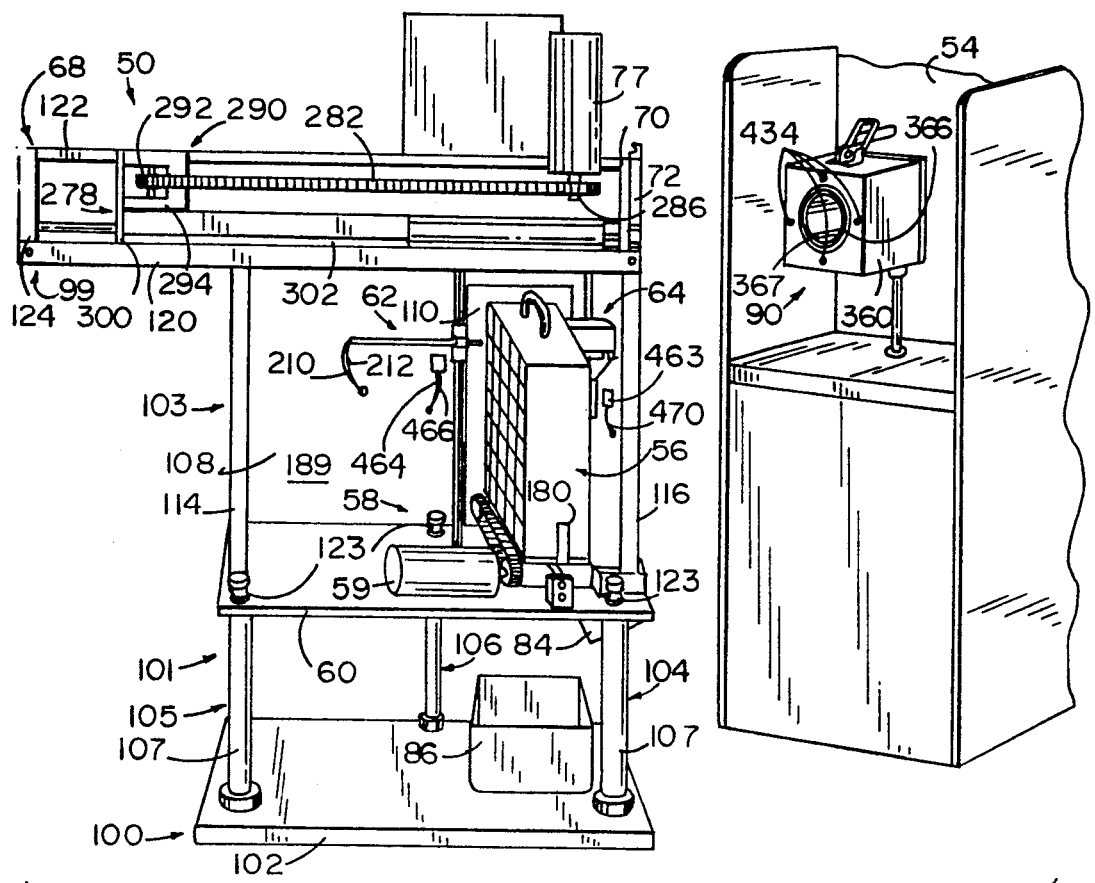
FIG. 1 is a front perspective view of an autoloader according to the invention and a fragmentary perspective view of a horizontal combustion furnace with which the autoloader is used.
Figure 2:
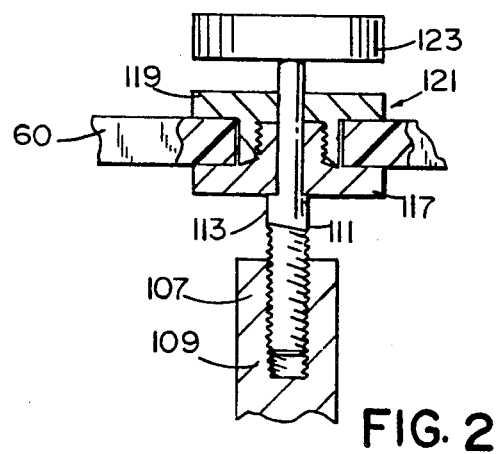
FIG. 2 is a partially cut-away front elevational view of a height adjustment mechanism for the autoloader according to FIG. 1 with the autoloader platform shown in fragmentary form.
Figure 5:
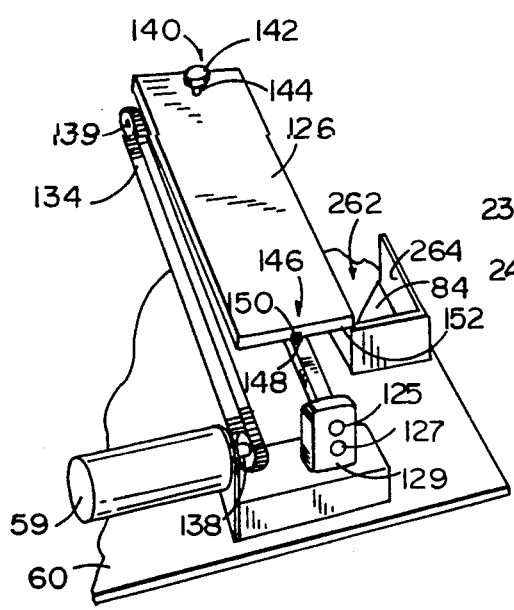
FIG. 5 is a top perspective view of a hotel carriage assembly for the autoloader according to FIG. 1, wherein the autoloader platform is shown in fragmentary form.
Figure 6:
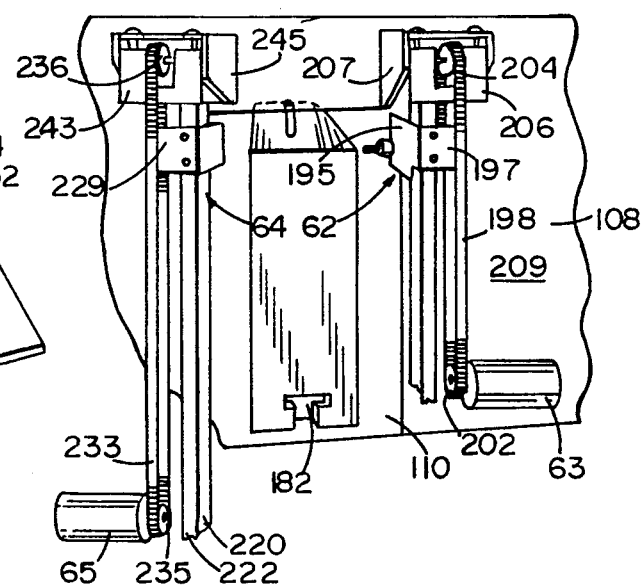
FIG. 6 is a perspective view of a push rod assembly, an elevator assembly and a boat hotel for the autoloader according to FIG. 1.
Figure 12:
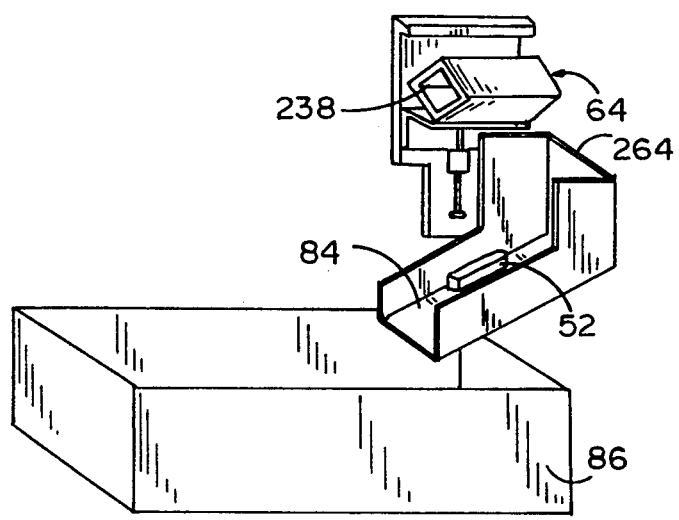
FIG. 12 is a fragmentary perspective view of the autoloader spent boat container according to FIG. 1 with the boat elevator at its lowest position.

With reference initially to FIG. 1, an autoloader 50 is illustrated which automatically loads boats 52 (FIG. 2) into an analyzer/furnace 54 (FIG. 1). The autoloader may be used with a commercially available Leco CNS2000 analyzer. The autoloader includes a boat hotel 56 (best illustrated in FIG. 3) which stores boats 52 having samples to be analyzed therein. Boat hotel 52 is mounted to a boat hotel carriage 58 (best illustrated in FIG. 5) which moves hotel 56 forward and backward on a platform 60 under the control of a motor 59. A pneumatic boat pusher 62 (FIG. 7) pushes boats 52 out of hotel 56 and onto a lower shelf 68 of an elevator 64. Boat pusher 62 is moved vertically by a DC motor 63 (FIG. 6). Elevator 64 is moved vertically by a DC motor 65. The boat elevator provides the vertical transportation of boats 52 within the autoloader. Elevator 64 includes a pneumatic tilter 79 (FIG. 8) for dispensing spent boats 52 into a spent boat container 86 (FIG. 12). A shoot 84 is positioned below elevator 64 for deflecting spent boats from elevator 54 into container 86.

Figure 21:
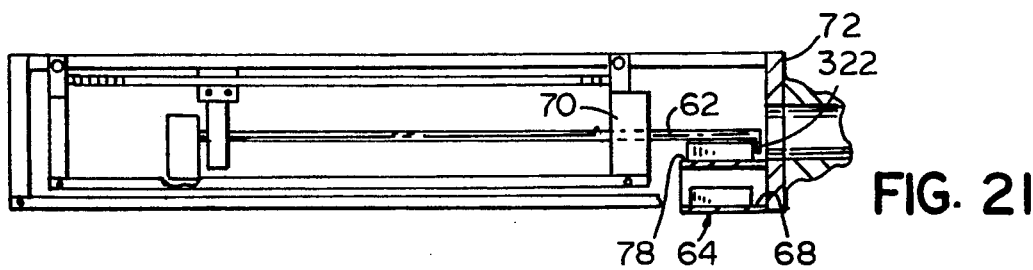
FIG. 21 is a front elevational view of a boat launch assembly according to FIG. 1, partially cut-away, with the boat retrieval arm placing a spent boat onto the upper position of the elevator.
Figure 23:
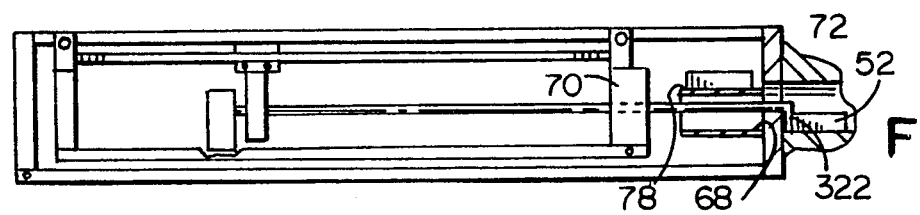
FIG. 23 is a front elevational view of the boat launch assembly according to FIG. 21 with the retrieval rod pushing the next boat off the elevator into the purge position of the furnace.
Figure 25:
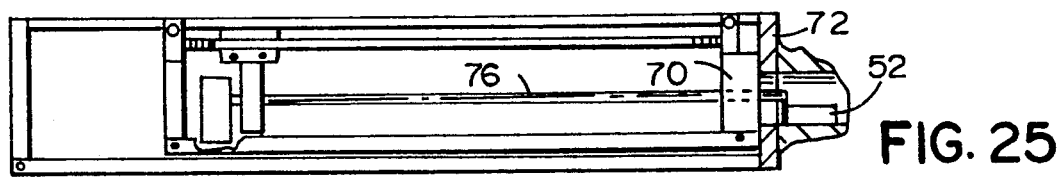
FIG. 25 is a front elevational view of the boat launch assembly according to FIG. 21 with the furnace sealing block in a sealed position and the retrieval rod in the rest position.
Figure 26:
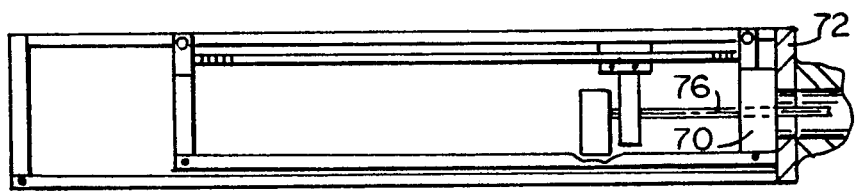
FIG. 26 is a front elevational view of the boat launch assembly according to FIG. 21 with the retrieval rod pushing the boat into the furnace according to FIG. 1.
Figure 27:
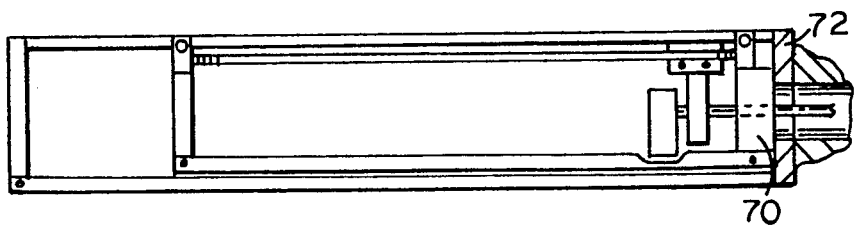
FIG. 27 is a front elevation view of the boat launch assembly according to FIG. 21 with the boat retrieval rod fully inserted into the furnace.

The autoloader includes a boat launch assembly 68 which seals a purge chamber 90 (FIG. 1) of analytical furnace 54 and provides horizontal transport of boats 52 within the analytical furnace and purge chamber. The boat launcher includes an autoloader furnace attachment block 72 for abutting contact with purge chamber 90. The boat launcher assembly also includes a furnace sealing plate 70 which is selectively moved to a sealing position abutting autoloader furnace attachment block 72. A boat retrieval rod 76 (FIG. 11) extends through sealing plate 70. The retrieval rod is moved laterally by a motor 77 for retrieving boats from analyzer/furnace 54 and loading the boats onto the top shelf 78 (FIG. 21) of elevator 64. The boat retrieval rod is also moved laterally to load boats 52 from the lower shelf 68 of elevator 64 into analyzer/furnace 54 (FIG. 23).

Somewhat more particularly, autoloader 50 includes a frame 100 (FIG. 1). The frame includes a lower frame section 101 and an upper frame section 103, and a boat launcher frame 99. Lower frame section 101 includes a base 102. A platform 60 of an upper frame section is supported by three leveling columns 104-106. Leveling columns 104-106 are vertically adjustable to align autoloader 50 with purge chamber 90. Each of leveling columns includes a cylindrical post 107 (FIG. 2) fixedly secured to base 102. Post 107 has a threaded aperture 109 at the top which receives one threaded end of a shaft 111. Shaft 111 includes a shelf 113 circumscribing the shaft. A grommet 121 includes lower half section 117 and an upper half section 119, each half section including threads for interconnecting the half sections through an aperture in platform 60. Shaft 111 is inserted through grommet 121 such that the lower half sits on shelf 113. A handle 123 is fixedly secured to shaft 111, and may be integrally formed therewith. Handle 123 is used to rotate shaft 111, which effects vertical movement of platform 60 relative to cylinder 117.

The upper frame section 103 includes platform 60, a back wall 108 and vertical supports 112 and 114. Back wall 108 (FIGS. 1 and 3) is connected to platform 60. Back wall 108 includes an opening 110 (FIG. 1) for receipt of hotel 56. Opening 110 allows the hotel to move through wall 108. A housing 112 (FIG. 3) is connected to back wall 108 by any suitable conventional means. Circuitry and pneumatic devices for controlling movement of the components of the autoloader are mounted within housing 112. Back wall 108, together with vertical supports 114 (FIG. 1) and 116, fixedly support launch assembly 68 on platform 60.

Figure 4:
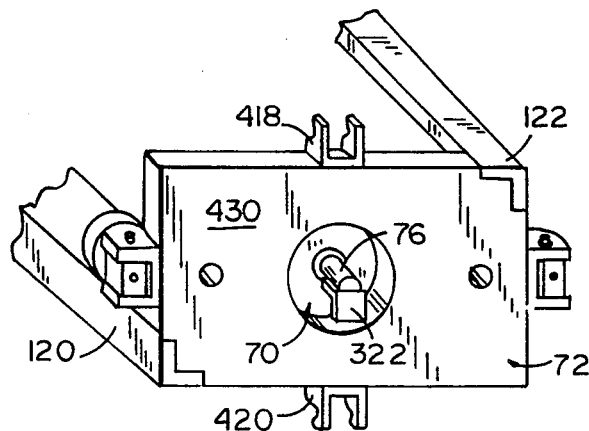
FIG. 4 is a fragmentary perspective view of a boat launch assembly for the autoloader according to FIG. 1.

Launch assembly 68 includes a frame 99. Frame 99 has a front beam 120 and a rear beam 122, each having an L-shaped cross section, as best illustrated in FIG. 4. Beams 120 and 122 may be formed from any suitable material, such as extruded aluminum. The beams extend between an end member 124 and autoloader furnace attachment block 72. End member 124 and attachment block 72 may be formed from any suitable material such as stainless steel or aluminum. The front and rear beams are mounted on end member 124 and autoloader furnace attachment block 72 by any suitable conventional method to form a rigid launch frame.

Figure 3:
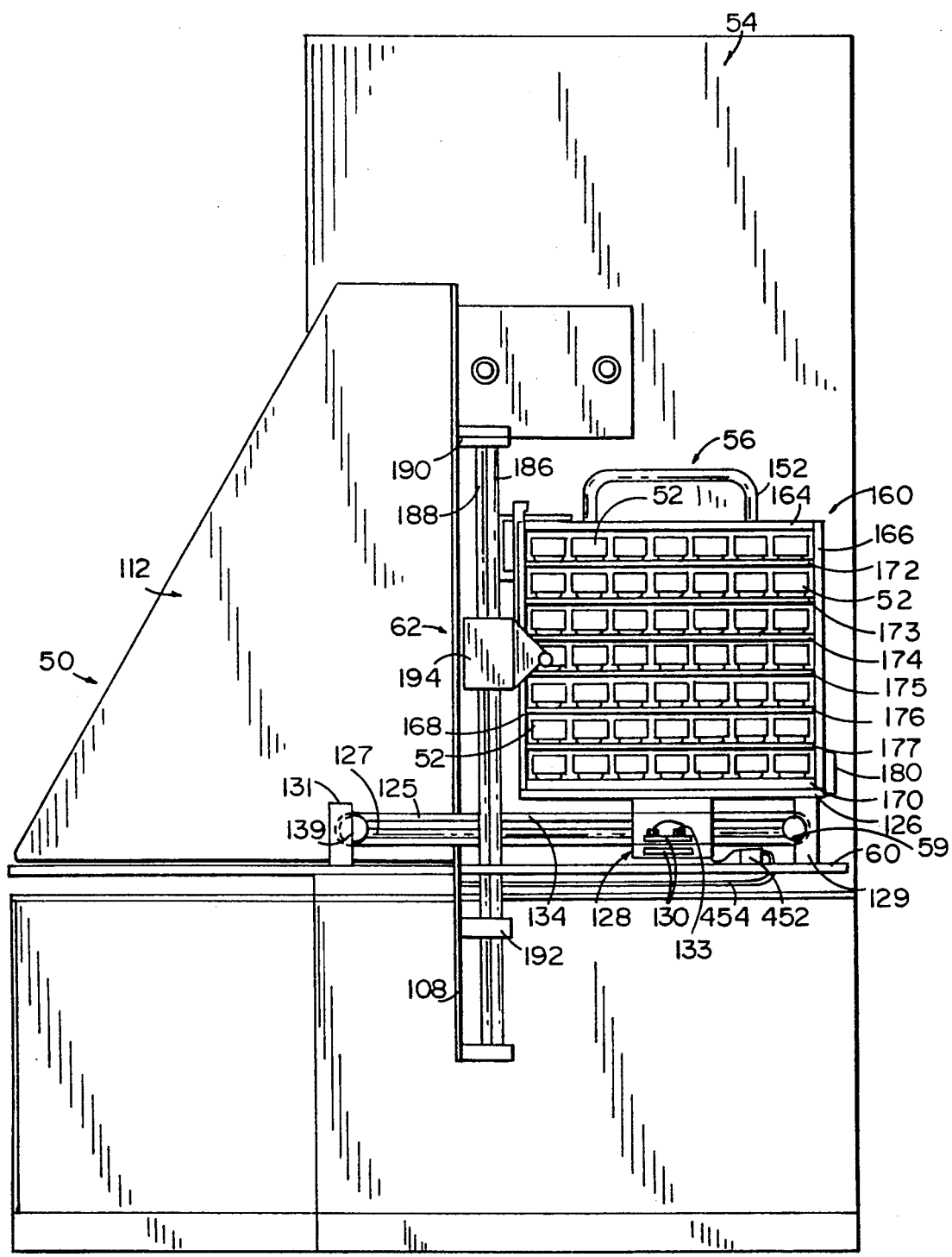
FIG. 3 is a side elevational view of the autoloader and furnace according to FIG. 1.

Still more particularly, autoloader 50 includes a boat hotel carriage assembly 58 (FIGS. 3 and 5) for movement on vertically stacked, juxtapositions guide rails 125 and 127. Opposite ends of guide rails 125 and 127 are mounted to platform 60 using mounting brackets 129 and 131. A guide rail trolley mechanism 128 is movingly attached to guide rails 125 and 127 in any suitable, conventional manner. A generally rectangular platform 126 is secured to trolley mechanism 128 using any suitable means, such as threaded fasteners (not shown). Trolley mechanism 128 also includes a clamp 130 which is fixedly connected to a timing belt 134 using threaded fasteners 133 (FIG. 3). The timing belt may be provided by any suitable belt such as a stainless cable with polyurethane. Trolley mechanism 128 moves with timing belt 134 on the guide rails 125, 127.

DC motor 59 is fixedly attached to platform 60 in any suitable conventional manner for moving timing belt 134. DC motor 59 is provided by any suitable, commercially available motor, such as a DC brushless gear motor with an optical encoder. The DC motor includes a shaft/sprocket 138. Timing belt 134 engages shaft/sprocket 138. The timing belt also engages a pulley 139 which is fixedly secured to platform 60. Motor 59 effects precise rotating movement of timing belt 134 on pulley 139 and shaft sprocket 138. The trolley mechanism 128 is clamped to belt 134 such that the trolley moves with the belt.

Platform 126 includes mounting devices for facilitating attachment of hotel 56 to platform 126. An orthogonally projecting post 140 is a first mounting device. Post 140 includes a disc 142 and a concentric smaller diameter rod 144. Rod 144 is attached to platform 126 by any suitable conventional means. Disc 142 is attached to an end of rod 144 and may be integrally formed with rod 144. A projecting anchor 146, having a head 148, defines a groove 150 between head 148 and end 152 of platform 126.

Boat hotel 56 includes a generally rectangular housing 160 (FIG. 3). Housing 160 includes a handle 152 extending from a top wall 164 thereof. A sidewall 166 and a sidewall 168 extend orthogonally from top wall 164. A bottom wall 170 extends between sidewalls 166 and 168. Hotel 56 also includes shelves 172-177 which extend parallel to top wall 164 and bottom wall 170 between sidewalls 166 and 168. The side walls are attached to top wall 164, bottom wall 170, and shelves 172-177 by any suitable construction, such as threaded fasteners inserted through the side walls and received in the horizontal walls/shelves. The shelves may contain ribs (not shown) which define storage positions on the shelves for boats 52. Each boat is accurately positioned when placed between two of such ribs. The housing may be made of any suitable material such as extruded aluminum. A hinged conventional snap fastener 180 (FIGS. 1 and 3) is mounted to sidewall 166 in any suitable conventional manner such as by threaded fasteners. Snap connector 180 may be provided by any suitable, conventional snap-connector which will engage anchor 146 (FIG. 5). A T-shaped recess 182 (FIG. 6) is provided in a wall 166 to receive post 140.

Autoloader 50 also includes a boat pusher 62 (FIGS. 1, 3 and 6) mounted for vertical movement on the back wall 108 such that it may be positioned adjacent boats 52 in different rows of hotel 56. Juxtaposed guide rails 186 (FIG. 3) and 188 are vertically mounted on back wall 108 to provide a track for the boat pusher. The guide rails are mounted to the front face 189 (FIG. 1) of the back wall 108 using mounting brackets 190 and 192. Guide rail mounting brackets 190 and 192 may be mounted to back wall 108 using any suitable conventional means such as threaded fasteners or welding. A trolley mechanism 194 (FIG. 7) securely engages guide rails 186 and 188. The trolley mechanism includes a bracket 195 (FIG. 6) which extends through opening 110. A clamp 197 is fixedly secured to bracket 195 and to a timing belt 198. Timing belt 198 may be provided by any suitable chain means such as a stainless cable with polyurethane. Vertical movement of the timing belt thus effects movement of trolley 194 upwardly and downwardly on guide rails 186 and 188.

A DC motor 63 includes a shaft/sprocket 202 extending outwardly therefrom for effecting movement of timing belt 198. Shaft/sprocket 202 includes teeth for engaging timing belt 198 which extends around shaft/sprocket 202 and a pulley 204. Pulley 204 is rotatably mounted to a block 206. Block 206 is mounted to a bracket 207 by any suitable conventional mean such as welding. Bracket 207 is mounted to the back face 209 of back wall 108 in any suitable conventional manner, such as by welding or using threaded fasteners.

The pneumatic push rod 62 includes a cylinder 208 (FIG. 7) and a push rod pin 209. The push rod cylinder 208 is mounted to bracket 195. The push rod cylinder is mounted orthogonally with respect to guide rails 186 and 188 such that push rod pin 209 will move orthogonally through hotel 56. Push rod cylinder 208 receives fluid control signals through tube 210 and 212 for moving push rod pin 209. Forward motion pneumatic control signals are received through tube 210 and withdrawal control signals are received through tube 212. The control signals may be received from any suitable source, such as a compressor or bottled air (not shown). The fluid control signals input to push rod cylinder 208 effect movement of push rod pin 209 through housing 56 such that boats 52 are pushed onto lower shelf 68 of elevator 64. When the control signal ceases, the push rod pin returns to its rest state which is the position illustrated in solid in FIG. 7.

Figure 9:
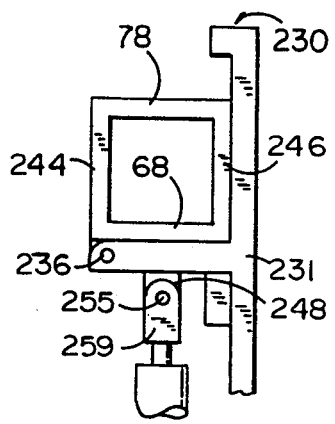
FIG. 9 is a fragmentary side elevational view of an elevator box shown its rest state.
Figure 10:
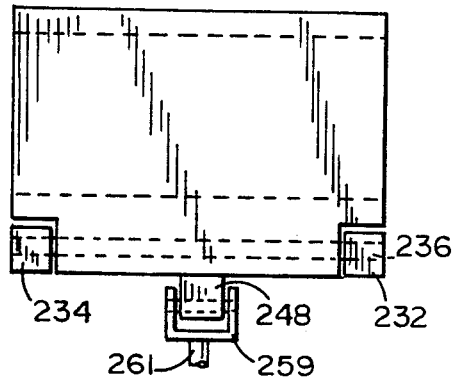
FIG. 10 is a fragmentary front elevational view of a box, arms and push rod of the elevator according to FIG. 9.

Elevator 64 is slidingly mounted on juxtaposed guide rails 220 (FIG. 6) and 222 which are mounted vertically to the front face 189 of back wall 108 using mounting brackets 224 (FIG. 7) and 226. Mounting brackets 224 and 226 are mounted to back wall 108 by any suitable conventional means, such as by welding or using threaded fasteners. A guide rail trolley mechanism 228 (FIG. 8) securely, movably engages rails 220, 222 for upward and downward movement of elevator 64 thereon. Trolley 228 includes a mounting bracket and clamp 229 (FIG. 6) which extends through opening 110 and is fixedly secured to a timing belt 233. Trolley mechanism 228 thus moves with timing belt 233. Timing belt 233 engages toothed sprockets 235 and 236. Sprocket 235 is supported on the shaft of D.C. motor 65. Sprocket 236 is rotatably secured to a block 243. Block 243 is mounted by any suitable conventional means to a bracket 245. Bracket 245 is mounted on the back face 209 of back wall 108 by any suitable conventional means such as welding or using threaded fasteners. The elevator includes a frame 230 (FIG. 8) attached to trolley mechanism 228 using any suitable conventional means such as threaded fasteners. Frame 230 includes a base 231 and integral arms 232, 234 projecting orthogonally therefrom. A pivot axle 236 extends through the distal ends of arms 232 and 234 (FIG. 10). A box 238 of elevator 64 is hingedly attached to pivot axle 236 and rests on arms 232, 234 in a rest state illustrated in FIG. 9. Box 238 includes a top shelf 78 and a bottom shelf 68. A front wall 244 and a back wall 246 extend orthogonally between top shelf 78 and bottom shelf 68. The ends of box 238 are open such that boats may be placed on and removed from lower shelf 68.

Figure 8:
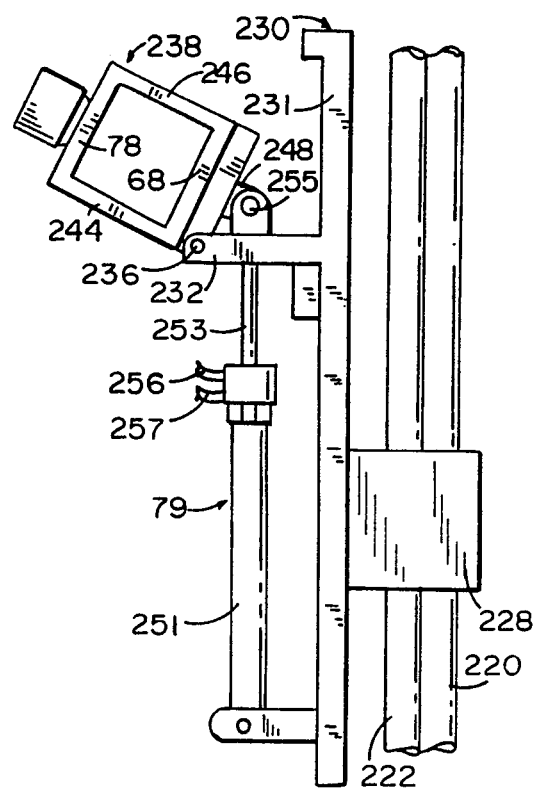
FIG. 8 is a side elevational view of an elevator for the autoloader according to FIG. 1, with the guide rails therefor shown in fragmentary form.

A foot 248 extends downwardly from bottom shelf 78 and includes a bore extending laterally therethrough. A pneumatic tilter 79 is connected to foot 248. Pneumatic tilter 79 includes a cylinder 251 and a pin 253. Pin 253 is attached to foot 248 by a U-shaped bracket 259 which is attached to end 261 of pin 253. An axle 251 extends through bracket 259 and foot 248. Box 238 pivots on axles 255 and 236 to move between the dump and rest positions, and thus to dump boats 52 from top shelf 78. End 263 of cylinder 251 is pivotally secured to outwardly projecting shoulders of a U-shaped bracket 256. An axle 274 extends through bracket 256 and cylinder 257 to provide a pivot point tilting rod 250 when the hotel is moved between the rest and the dump positions. Cylinder 251 receives control signals through tube 256 for moving pin 253 from its rest posit to its fully extended position, and thus tilting box 238 (FIG. 8). Fluid control signals for returning pin 253 and elevator box 238 to the rest position are input through a tube 257.

A spent boat container 86 (FIG. 1) is positioned on base 102 below elevator 64 to receive spent boats 52 dumped from the top shelf 78 of the elevator. The spent boat container 86 may be provided by any suitable, conventional container for receipt of hot boats. The container is positioned below an opening 262 (FIG. 5) in platform 60. A guard rail 264 (FIG. 12) preferably circumscribes, a extends through, opening 262 to direct boats to shoot 84. Shoot 84 deflects boats into container 86. Shoot 84 and guard rail 264 may be of any suitable construction, such as integrally formed of a suitable metal. Shoot 84 may alternatively be provided by any suitable means such as a single metal plate angled toward container 86 or a pair of plates having a V-shaped profile and an opening at the bottom. The container provides a collection and cooling facility for spent boats unloaded from the furnace by the autoloader. The container preferably has sufficient capacity to hold all the containers in hotel 56.

Figure 11:
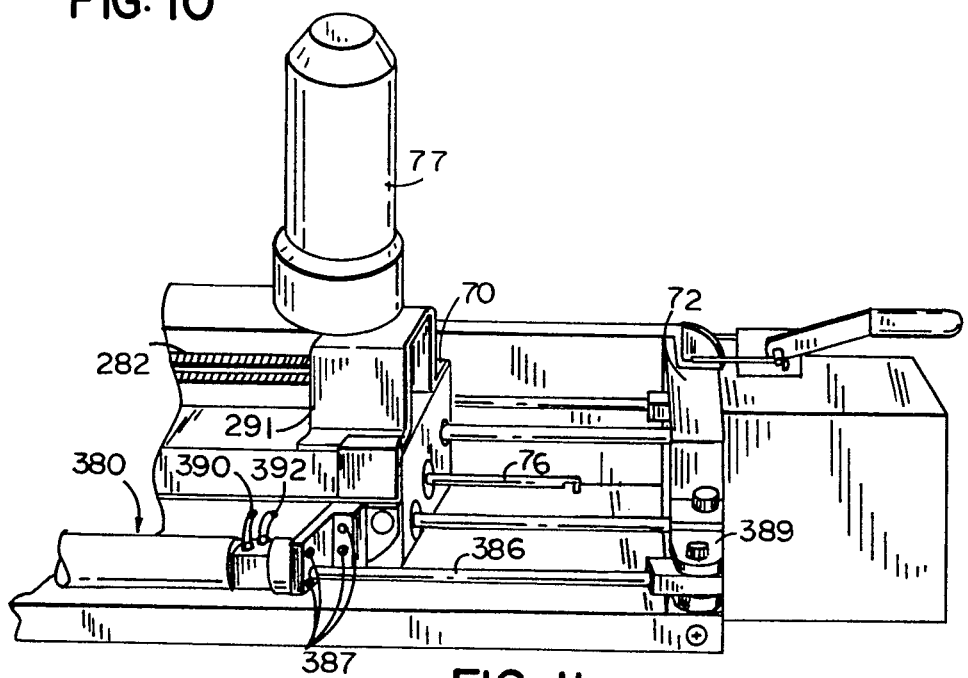
FIG. 11 is a fragmentary perspective view of a boat launch assembly for the autoloader according to FIG. 1.

Launch assembly 68 includes horizontal, laterally spaced guide rails 279 (FIG. 13) and 281 extending between end block 124 and autoloader attachment block 72. The guide rails are fixedly mounted on block 72 and member 124 by any suitable, conventional means, such as by threaded fasteners secured to the ends on the rods. A boat retrieval rod and sealing block carriage 278 is supported for lateral movement on rails 279 and 281. Carriage 278 includes a guide block 300 and furnace sealing plate 70. Guide block 300 and furnace sealing plate 70 are connected by beams 302 and 304. The guide blocks and beams provide a rigid carriage assembly for movement on the guide rails A motor 77 (FIG. 1), including a shaft and sprocket 286, is mounted to furnace sealing plate 70 (as best illustrated in FIG. 11). The motor may be attached using a U-shaped mounting bracket 291 assembled to furnace sealing plate 70 in any suitable, conventional manner, such as by welding or use of threaded fasteners (not shown). A pulley 290 (FIG. 1), including a sprocket 292 and a pulley block 294, are attached to guide block 300. Sprocket 292 is rotatably supported on the pulley block 294. Block 294 is, in turn, connected to guide block 300 by conventional means, such as by welding or using threaded fasteners. Sprockets 292 and 286 are operably connected by a timing belt 282, such that the timing belt rotates on sprockets 286 and 292 when motor 77 operates.

A guide rail support block 316 is also slidingly engaged on spaced guide rails 279 and 281. A clamp 314 (FIG. 7) is attached to support block 316 by conventional means, such as by welding or threaded fasteners. Clamp 314 fixedly clamps onto timing belt 282. Timing belt 282 may be provided by any suitable, conventional means such as a stainless cable and polyurethane. Support block 316 moves relative to the retrieval rod and sealing plate carriage 278 when motor 77 moves timing belt 282 moves.

Figure 16:
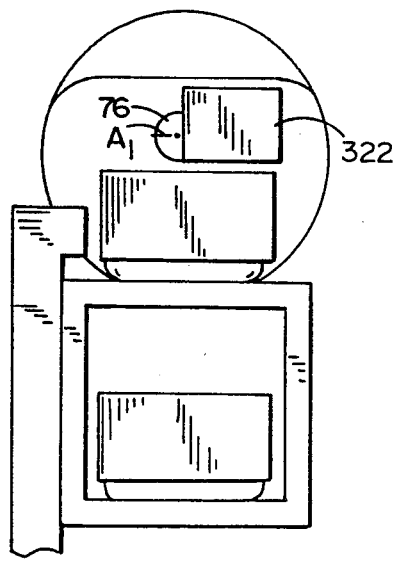
FIG. 16 is a side elevational view of the elevator, the boat retrieval rod and the boat according to FIG. 15, with the retrieval rod shown in its "up" position.
Figure 15:
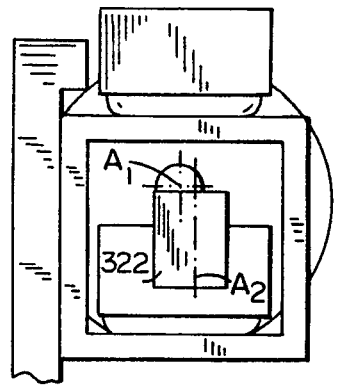
FIG. 15 is a fragmentary side elevational view of an elevator, a boat retrieval rod and boat according to FIG. 1, with the retrieval rod shown in its "down" position.
Figure 14:
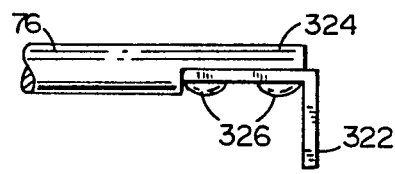
FIG. 14 is a fragmentary side elevational view of a boat retrieval rod and hook for the boat launch assembly according to FIG. 13.

The boat retrieval rod 76 (FIG. 3) passes through support block 316 and is secured to a pneumatic rotor 317. Boat retrieval rod is preferably constructed of 303 stainless steel. Rotor 317 is fixedly mounted on support block 316. The boat retrieval rod also extends through furnace sealing plate 70. The retrieval rod includes an L-shaped hook 322 (FIG. 14) on the distal end 324. The hook is preferably constructed from sheet stainless steel bent to be L-shaped. The hook may be secured on the end of rod 76 by any suitable conventional means such as threaded fasteners 326. The threaded fasteners are preferably constructed of stainless steel. The center axis of hook 322 is preferably laterally offset from the center axis A1, of rod 76. Accordingly, the hook 322 may be wider than rod 76 to provide a wide impact area for engagement with boat 52 in the down position (FIG. 15), and move out of the way of boat 52 when rod 76 rotates to the up position illustrated in FIG. 16.

The boat retrieval rod 76 is rotated under the control of a pneumatic rotary actuator 400. Rotor 400 provides 90° rotation of rod 76. Rotator 400 is fixedly mounted to guide block 316 by any suitable, conventional means.

Rotor 400, guide block 316 and rod 76 thus slide longitudinally simultaneously to move the retrieval rod into and out of analyzer/furnace 54. The rotor receives clockwise rotation pneumatic control signals through an input tube 401 and counter clockwise pneumatic control signals through a return tube 403.

Figure 17:
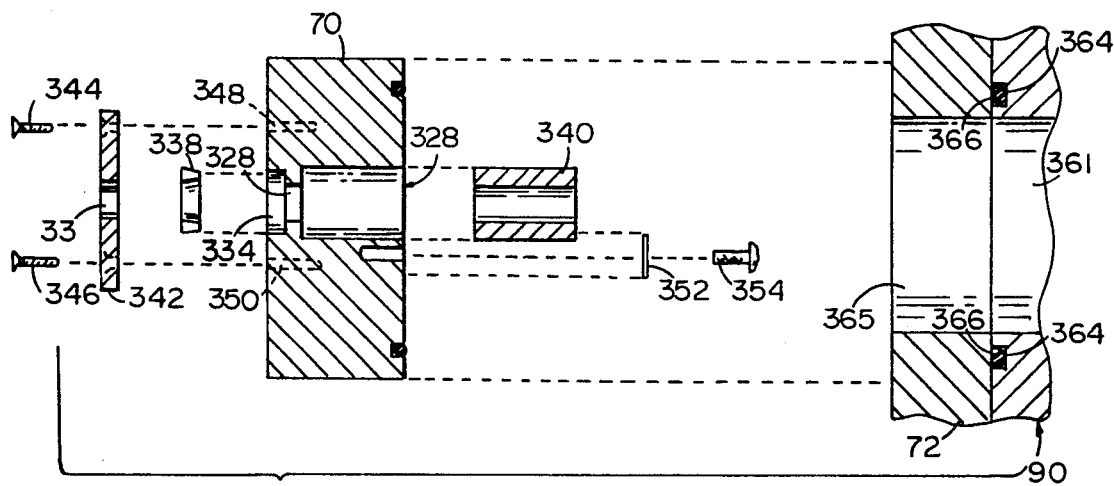
FIG. 17 is an exploded, partially fragmentary sectional view of the sealing block, a furnace attachment block, and a purge chamber according to FIG. 1.
Figure 18:
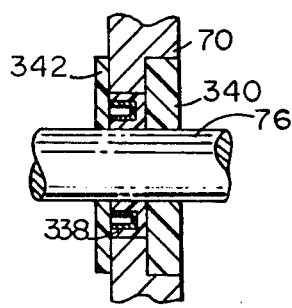
FIG. 18 is a fragmentary, partially cross sectional side elevational view of the push rod with the sealing block according to FIG. 17.

The furnace sealing plate 70 includes a bore 328 (FIG. 17) extending transversely therethrough for receipt of retrieval rod 76 and sealing members therefor. Retrieval rod 76 and furnace sealing plate 70 are sealed as illustrated by FIG. 18 to prevent the passage of gas through the sealing plate. The seal is provided by a Teflon spring seal 338 (FIGS. 17 and 18) a bushing 340 and a mounting bracket 342. A counterbore 334 is concentric with bore 328 and receives teflon spring seal 338 when it is inserted into counterbore 334. Mounting bracket 342 is attached to sealing plate 70 to secure teflon seal 338 in counter bore 334. Mounting bracket 342 may be constructed of any suitable material such as brass. The mounting bracket may be secured by any conventional means such as by threaded fasteners 344 and 346 which are received through bracket 342 and secured in threaded apertures 348 and 350. Sealing plate 70 also includes a counterbore 336 which is concentric with bore 328 and receives bushing 340. The bushing may be constructed of any suitable material such as aluminum. A low friction tape (not shown), such as a teflon or floral polymer tape, is preferably attached to the inside diameter of disk 340 such that it is positioned between disc 340 and rod 76. Disc 340 is secured in counterbore 336 by any conventional means, such as by washer 352 and threaded fastener 354. Threaded fastener 354 is received in a threaded aperture 356 in sealing plate 70. Sealing plate 70 also includes a circular channel 358. Channel 358 receives an 0-ring 359. 0-ring 359 provides a seal between sealing plate 70 and autoloader furnace attachment block 72.

Figure 13:
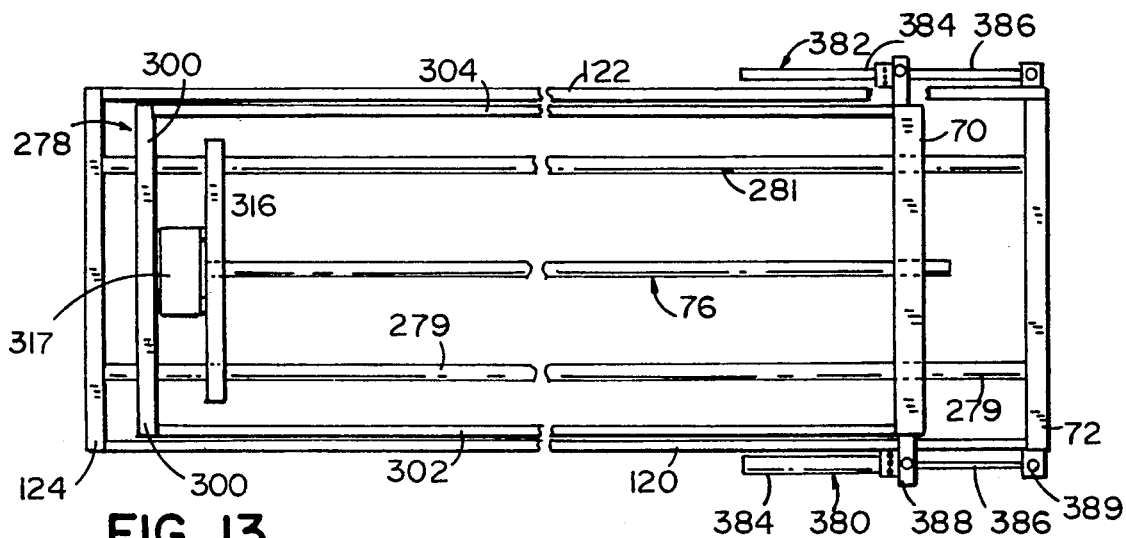
FIG. 13 is a top plan view of a boat launch assembly for the autoloader according to FIG. 1.
Figure 24:
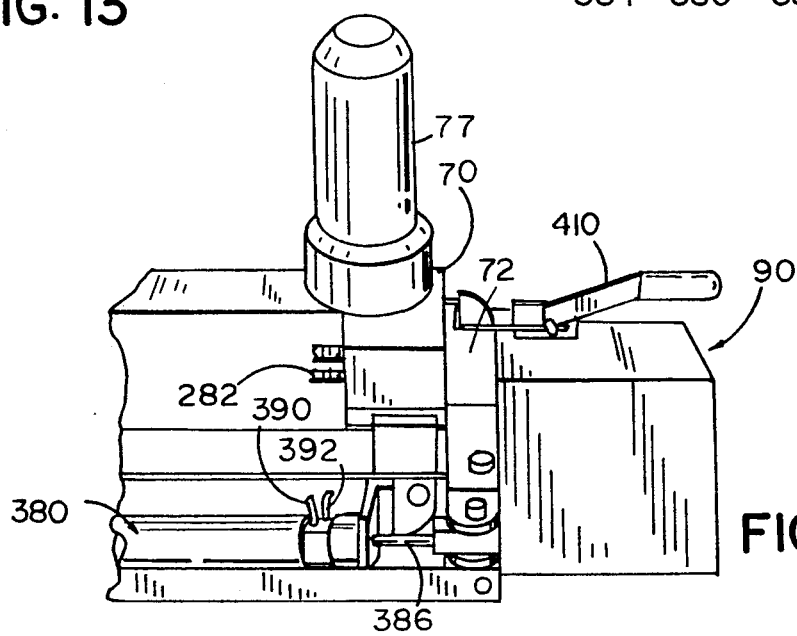
FIG. 24 is a fragmentary front perspective view of the boat launch assembly according to FIG. 11 with the furnace sealing block, the autoloader attachment block and the purge chamber in abutting position.
Figure 19:
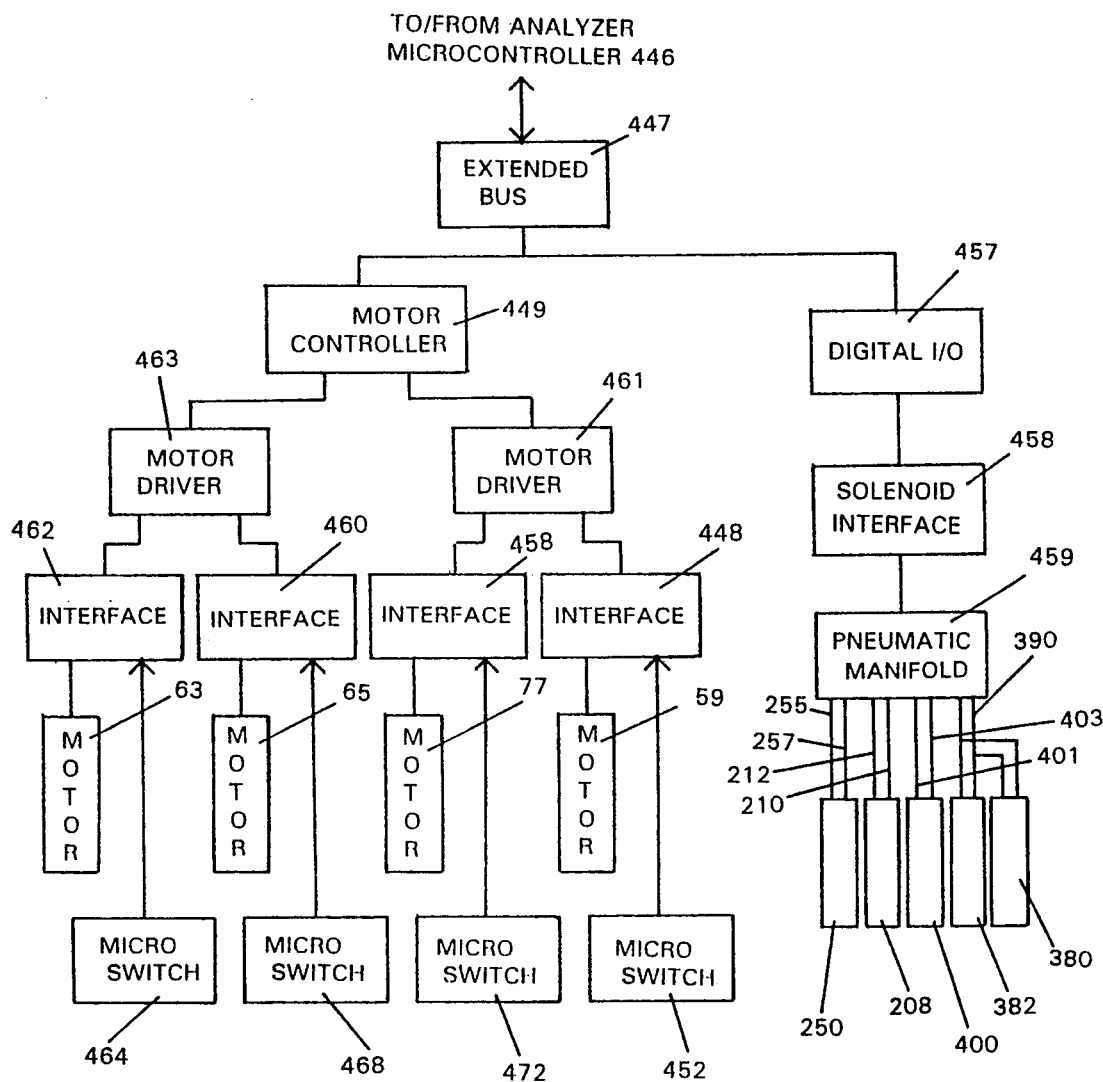
FIG. 19 is a circuit schematic in block diagram form of an electronic control circuit and pneumatic control circuit for the autoloader according to FIG. 1.

The sealing plate 70, with its associated carriage assembly, is moved between an open position and a closed position by pneumatic devices 380, 382 (FIGS. 11 and 13). Pneumatic devices 380 and 382 each include a cylinder 384 and a rod 386. Cylinder 384 is secured to block 70 by any suitable, conventional means such as by a L-shaped bracket 388 (FIG. 11) mounted to the cylinder and block 70 by threaded fasteners 387. Rod 386 is secured to autoloader furnace attachment block 72 by a U-shaped bracket 389. Bracket 389 is secured to block 72 by any suitable means such as threaded fasteners (not shown). The bracket is secured to rod 386 by conventional male and female threaded fasteners. The pneumatic cylinder receives fluid control signals from a control signal source 470 (FIG. 19). Control signals for moving plate 70 from the open to the closed position are input through a supply tube 390 (FIG. 11). Control signals for moving plate 70 from the closed to the open position are input through a tube 392.

Purge chamber 90 is secured to face 430 (FIG. 4) of furnace attachment block 72. The purge chamber includes housing 360 having a central bore 361 aligned with a furnace tube 362 (FIG. 7) of analyzer/furnace 54 and a bore 365 through sealing plate 72. The purge chamber also includes a circumscribing channel 364. An 0-ring 366 is received in channel 364 for sealing the purge chamber against autoloader furnace attachment block 72.

The purge chamber 90 is locked into engagement with autoloader attachment block 72. To accomplish a secure lock with a tight seal, a top snap-lock 410 and a bottom snap-lock 412 are mounted on a top wall 414 and a bottom wall 416 of the purge chamber 90. The snap lock may be provided by any suitable, commercially available snap lock. The snap locks are connected to purge chamber 90 by any suitable conventional means such as by threaded fasteners or welding. A U-shaped bracket 418 for receipt of snap connector 410 is mounted at the top of block 72 by any suitable conventional means such as threaded fasteners. A U-shaped bracket 420 is mounted to the bottom of block 72 for receipt of snap-lock 412. The bracket may be mounted by any conventional means such as by threaded fasteners or welding.

The control circuit for the autoloader will now be described with reference to FIG. 19. The autoloader is controlled by a microcontroller 446. Microcontroller 446 is preferably implemented by a personal computer used to control the analyzer/furnace 54, although it may be implemented using any commercially available microcontroller. The microcontroller is connected to an extended bus interface 447. Interface 447 directs control signals from microcontroller 446 to a motor controller 449 or a digital input/output (I/O) circuit 457.

Motor controller 449 is responsive to control signals from extended bus 447 to control motor driver 463. Motor driver 463 controls interface 462 to selectively supply positive or negative power to motor 63. Motor driver 463 also controls interface 460 to selectively supply positive or negative power to motor 65. The interface 462 is also connected to microswitch 464. Interface 462 is responsive to control signals from microswitch 464 to supply control signals, via motor driver 463 and motor controller 449, to extended bus 447 indicating when microswitch 464 is closed. Interface 460 is similarly connected to microswitch 468 and supplies a control signal via motor driver 463 and 449 to extended bus 447 which indicate when microswitch 468 is closed.

Motor driver 461 is connected to interface 458 and interface 448. Interface 458 is responsive to control signals from motor driver 461 to selectively supply positive or negative power to motor 77. The interface provides positive or negative power to the motor to control the direction of motor operation. Interface 448 is responsive to control signals from motor driver 461 to provide positive or negative power to motor 59. Motor 59 is responsive to positive and negative power supply to move in a forward and backward direction, respectively. Interface 458 is connected to microswitch 472 and supplies control signals to extended bus 447 via motor controller 449 and motor driver 461 to indicate when the microswitch is closed. Interface 448 is connected to microswitch 452 to receive a control signal therefrom. The control signals 452 are supplied via interface 448 and motor driver 461 to extended bus 447 which indicate when microswitch 452 is closed.

Microswitches 452, 464, 468 and 472 are used to set the zero position for trolley mechanism 128, trolley mechanism 194, trolley mechanism 228, and support 316, respectively. Upon power up, each of these devices will move to the position which closes its associated microswitch. All the stop positions of each of the devices 128, 194, 228 and 316 are programmed relative to the microswitch position after the autoloader is manufactured. By using the microswitches and positioning which is relative to the microswitches, precise stop locations for each of the devices is reliably provided each time the autoloader control system is powered up.

The pneumatic devices are controlled by a pneumatic source 470. Source 470 includes digital I/O 457 receives digital signals from extended bus 447 and outputs control signals to a solenoid interface 458. Solenoid interface 458 is connected to a pneumatic manifold 459 such that a plurality of solenoid control the opening and closing of respective valves connected to each one of tubes 390, 392, 401, 403, 210, 212, 255 and 257. Each of the manifolds is thus responsive to a respective solenoid to output air to its associated tube.

When the autoloader is initially connected to analyzer/furnace 54, a face 430 (FIG. 4) of attachment block 72 must be parallel with a face 432 (FIG. 1) of purge chamber 90. Additionally, bore 365 (FIG. 17) of furnace attachment block 72 must be aligned with bore 361 of purge chamber 90. The level adjusting columns 104, 105 and 106 are adjusted to provide appropriate orientation using columns 104, 105 and 106. The axial alignment of bores 361 and 365 assisted by posts 434 projecting outwardly from face 432 of purge chamber 90. The posts are provided on purge chamber 90 such that when attachment face 72 is positioned between all four posts, the central bores 361 and 365 are aligned. It is important that these bores be aligned so that boats 52 may slide between elevator 64 and analyzer/furnace 54.

The operation of the autoloader will now be described. Initially, when the system is set up, the technician programs the stop positions for each of the motorized control mechanisms. The stop positions for each mechanism are programmed by measuring the distance between each stop position and the microswitch zeroing position associated with each device. Following power up, the microcontroller moves each device to its zero position, and then moves each device to its initial position for the loading sequence.

Figure 20A:
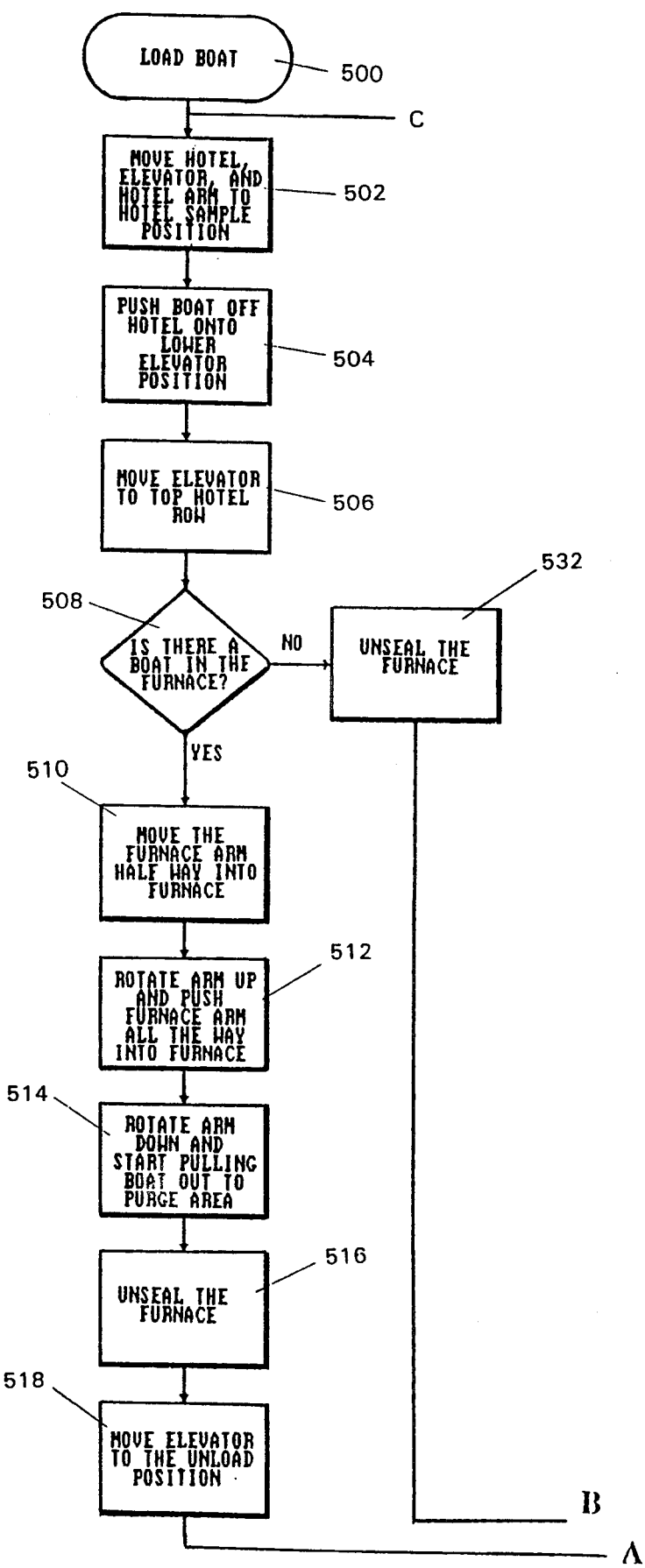
FIG. 20A and FIG. 20B are a flow diagram of the control circuit according to FIG. 19.
Figure 20B:
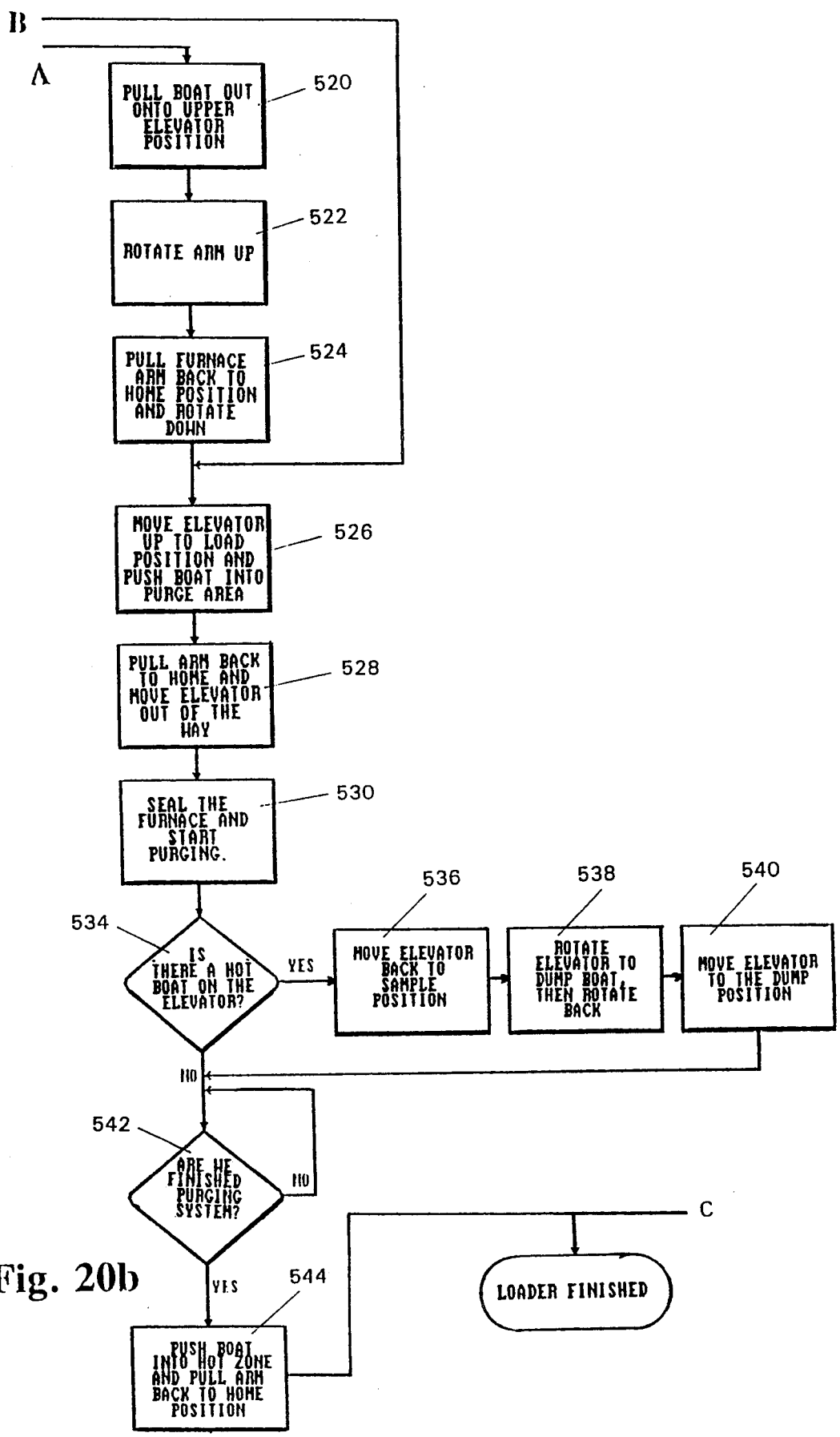

The operation of the system will now be described with reference to FIGS. 20A and 20B. Initially, hotel 56 is loaded with sample boats 52 as indicated in box 500. After it is loaded, an operator mounts hotel 52 on platform 126. To mount the hotel, post 140 is inserted into recess 182 in wall 166 of hotel 56. Snap connector 180 is inserted over post 146 and the connector is locked. The operator then initiates a loading sequence. In the loading sequence, the microcontroller 446 transmits a control signal to motor 59 through interface circuit 448 such that the hotel is moved to the column of the next sample to be loaded into the furnace (e.g., the farthest left column if the sample is in the upper left hand corner of hotel 64). The microcontroller also transmits control signals to motors 63 and 65 via interface circuits 458 and 460, respectively, such that the hotel and the elevator move simultaneously to the row associated with the next sample (e.g., the first row if the sample is in the upper left-hand corner). As indicated by box 502. The microcontroller then transmits an electronic signal to pneumatic source 460, which outputs a fluid control signal to cylinder 208 of pneumatic push rod 62. Responsive thereto, pin 209 of pneumatic drive 208 pushes a boat 52 out of the hotel and into the lower elevator shelf 68 as indicated in block 506. Microcontroller 446 then transmits a control signal to motor 65 which effects lifting of elevator 64 to the top row of the hotel if the elevator is not in that position already.

The microcontroller then determines whether a boat 52 is currently in the furnace as indicated in decision block 508. Because the analyzer/furnace personal computer is used to control the autoloader, the computer has boat status information stored therein. If a sample was analyzed, but the boat associated therewith was not removed, the microcontroller knows that a boat is in the furnace. If a boat is currently in the furnace, the microcontroller outputs a control signal to interface 462 which controls motor 77 to move the boat retrieval rod halfway into the furnace as indicated in block 510. The microcontroller then transmits a control signal to pneumatic source 460 which controls rotor 400 to rotate the retrieval rod 76 and hook 33 to the up position illustrated in FIG. 16. The microcontroller then transmits a control signal through interface circuit 462 to motor 77 such that push rod 76 is controlled to move all the way into furnace 54, as indicated in block 512. The microcontroller then transmits a control signal to pneumatic source 470 which outputs a fluid control signal to pneumatic drive 400 which effects rotation of hook 322 to the "down" position illustrated in FIG. 16. The microcontroller then transmits a control signal to interface 462 which causes motor 77 to pull the boat retrieval rod 76 and boat 52 out of the furnace and into the boat purge chamber 90 as indicated in block 514.

Microcontroller 446 then transmits a control signal to the pneumatic source 470, responsive to which the pneumatic source transmits a fluid control signal to pneumatic drives 380, 382. The pneumatic drives move the furnace sealing plates to the released position illustrated in FIG. 21, as indicated in block 516. The microcontroller then transmits a control signal to motor 65 through interface 458 responsive to which elevator 64 is moved to the unload position illustrated in FIG. 21, as indicated in block 518. In the unload position, shelf 68 is aligned with bores 361 and 365. Microcontroller 448 then transmits a control signal to motor 77 via interface 462 such that the motor and rod 76 pull boat 52 unto shelf 78, as indicated in block 520. The microcontroller then transmits a control signal to source 470, which outputs a fluid control signal to pneumatic rotor 400. The pneumatic rotor rotates hook 322 90° to the up position, as indicated in block 522. The microcontroller then transmits a control signal to motor 77, through interface 462, responsive to which motor 77 pulls retrieval rod 76 back to the home position illustrated in FIG. 8. Microcontroller 446 then transmits a control signal to pneumatic source 470 which outputs a fluid control signal to pneumatic rotor 400, responsive to which hook 322 is rotated 90°, as indicated in block 524.

Figure 22:
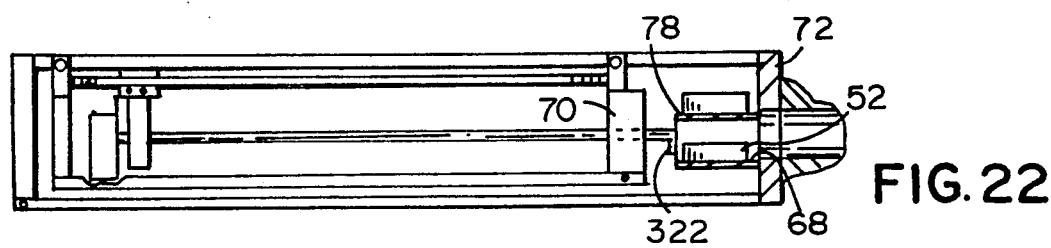
FIG. 22 is a front elevation view of the boat launch according to FIG. 21 with the retrieval rod in a rest position.

The microcontroller 446 then transmits a control signal to motor 65 through interface 458 which effects movement of elevator 64 to the load position illustrated in FIG. 8, as indicated in block 526. In the load position, shelf 68 is aligned with bores 361 and 365. Microcontroller 446 also transmits a control signal to motor 77 through interface 460, responsive to which, rod 76 and hook 322 push boat 52 into purge chamber 90. Microcontroller 446 also transmits a control signal to source 470 responsive to which the rotor 400 rotates rod 76 and hook 322 to the up position. The microcontroller then transmits a control signal to motor 77, responsive to which the boat retrieval rod 76 is moved back to the home position, which is illustrated in FIG. 22. The microcontroller then transmits a control signal to motor 65 via interface 460, responsive to which elevator 64 is lowered to a position where it will not interfere with the movement of furnace sealing plate 70 into abutment with autoloader furnace attachment block 72, as indicated in block 528. The microcontroller 446 then transmits a control signal to pneumatic source 470, responsive to which fluid control signals are input to pneumatic drivers 380 and 382 which push sealing plate 70 into secure engagement with autoloader furnace attachment block 72. The analytical furnace 54 will then effect purging of the purge chamber 90 by flushing the air in chamber 90 through the analytical system as indicated in block 530.

If it was determined in decision block 508 that a boat is not in the furnace, the microcontroller transmits a control signal to pneumatic source 470. Pneumatic source 470 transmits a fluid control signal to pneumatic drives 380 and 382, which moves the sealing plate 70 to the released position, as indicated in block 532. The program then proceeds to block 526. In decision block 534, the microcontroller determines whether a boat is on shelf 78 of elevator 64. If a boat is on shelf 78, a control signal is transmitted to motor 65 through interface 460 to effect movement of elevator 64 to its lowest, dump position as indicated in block 536. As indicated in block 536, the microcontroller then transmits a control signal to pneumatic source 470, responsive to which a fluid control signal is input to pneumatic tilter 79. Pneumatic tilter 79 pushes pin 253 upwardly causing rotation of box 238. The boat 52 on top shelf 78 is dropped from the elevator shelf such that it is deflected off shoot 84 into spent boat container 86. The microcontroller then inputs a control signal to input source 470 which outputs a control signal to tilter 79 causing the elevator to return to its rest state as indicated in block 538. The microcontroller then transmits a control signal to motor 65 through interface 460, responsive to which elevator 64 is moved to the next sample position as indicated in block 540. Simultaneously with movement of elevator 64 to the next sample position, pusher 62 is moved to the next row if the next sample is in a different row than the current sample in the furnace.

The microcontroller then determines whether the purge chamber 90 is purged as indicated in block 542. The microcontroller, which controls analyzer furnace 54 as described above, waits until the purge is complete, as indicated in block 542 before pushing the boat all the way into the furnace. The microcontroller then controls motor 77 to move the retrieval rod 76 such that the boat in the purge chamber is moved all the way into the furnace as indicted in block 544. The microcontroller then transmits a control signal to pneumatic rotor 400 through control 470, which effects rotation of the retrieval arm to the up position. The microcontroller then transmits a control signal to motor 77 which pulls the boat retrieval arm back to the home position such that hook 322 is positioned in purge chamber 90.

The microcontroller may be programmed to load any number of samples, up to the maximum number that the hotel will hold. The autoloader empties the hotel from left to right, emptying each row before moving to the next row. Accordingly, after each sample is removed, the hotel is moved to the next column. Alternatively, the microcontroller may be programmed to empty each column before moving to the next adjacent column. Of course, the microcontroller may be programmed to empty the samples in any order. Additionally, where the microcontroller is implemented using the analyzer furnace's personal computer. It is envisioned that the user would input the number of samples to be tested into the personal computer. The personal computer would display the positions where samples are to be loaded based upon the user wants to test.

Accordingly, it can be seen that an autoloader is disclosed which provides efficient loading of a plurality of samples into a analyzer/furnace one at a time, as well as unloading of the furnace after each sample is tested. The autoloader provides a sealing mechanism which allows for the introduction of the sample and subsequent sealing of the furnace to prevent introduction of atmospheric nitrogen during combustion and analysis. The system includes a mechanism which pushes a sample and a sample container into the furnace hot zone, retracts to a cooler region of the furnace during analysis, and then returns to the hot zone to retrieve the used container. Additionally, the system provides a method of delivering a spent, hot boats (having a temperature of approximately 800° C.) into a container where it will cool to room temperature and then may be reused or thrown away.

It will become apparent to those skilled in the art that modifications to the preferred embodiment of the invention as described herein can be made without departing from the preferred embodiment of the invention as described herein. For example, hydraulic control system or electric motors may be substituted for the pneumatic devices utilized in the autoloader. Additionally, the maximum capacity of the hotel could be greater than or less than forty-nine. These and other modifications to the present invention can be made without departing from the spirit or scope of the invention as defined by the appended claims.

The embodiments of the invention in which an exclusive property or privilege is claimed are defined as follows.

We claim:

1. An automatic sample loader for use with an analytical combustion furnace having a horizontal combustion tube comprising:
   a first frame member comprising a first horizontal plate vertically separated from a second horizontal plate by a plurality of vertical column members;
   a guide rail mounted on said first horizontal plate;
   a first carriage member movably mounted on said guide rail;
   a hotel member removably mounted on said carriage member, said hotel member comprising a frame having a top and a bottom member vertically spaced by attached end members with a plurality of vertically spaced horizontal plates connected at each end to said end members for carrying a plurality of combustion tools;
   motor means for moving said carriage member;
   a second frame member attached to and vertically spaced above said first frame member;
   a pair of horizontally spaced vertical end plates on said second frame member with one of said end plates having an aperture therein;
   a pair of spaced horizontal guide rods supported by said end plates;
   a second carriage member movably supported on said guide rods, said second carriage member comprising a furnace seal member having an aperture therein and a guide member spaced from said furnace seal member;
   a rotary actuator support member on said guide rods, and a rotary actuator member carried on said rotary actuator support member;
   a motor on said second carriage member for reversibly moving said rotary actuator support member;
   a boat retrieval rod supported by said rotary actuator member, said boat retrieval rod extending through said furnace seal member, a hook member on the distal end of said boat retrieval rod, said rotary actuator member for reversibly rotating said boat retrieval rod and hook member from a first position where said hook member extends horizontally to a second position where said hook member extends downwardly;
   a first vertical guide rail mounted on one side of said first carriage ember;
   a first actuator member movably supported on said first vertical guide rail, said actuator member comprising a pneumatic cylinder having a horizontally extendible rod member for pushing combustion boats from said hotel member;
   motor means for reversibly vertically moving said first actuator member on said first vertical guide rail;
   a second vertical guide rail mounted on the other side of said first carriage member; and
   an elevator means movably mounted on said second vertical guide rail for receiving combustion boats from said hotel member and for delivering said combustion boats to a position where said combustion boats can be pushed by said boat retrieval rod.

2. A sample loader for a horizontal analytical combustion furnace comprising:
   a frame member for attachment to the horizontal combustion furnace comprising
   a first end plate having an aperture,
   a second end plate spaced from said first end plate, and
   a pair of spaced parallel guide rods joining said first and second end plates together;
   a furnace seal member having an aperture therein movably supported on said spaced guide rods;
   a closure member for said furnace seal member;
   reversible means for moving said furnace seal member into a sealing position and for moving said moving said seal member away from said said sealing position;
   a carriage member movably supported on said guide rods;
   a rotary actuator on said carriage member;
   a boat retrieval rod operatively connected to said rotary actuator and extending through said closure member in said furnace seal member, said boat retrieval rod having a hook on the end thereof remote from said rotary actuator, said rotary actuator reversibly moving said hook on said boat retrieval rod from an inoperative to an operative position; and
   a motor mounted on said frame for reversibly moving said carriage member.

3. A sample loader as set forth in claim 2, wherein said closure member comprises:
   a bearing member for closing a combustion furnace side of said aperture in said furnace seal member around said boat retrieval rod.

4. The sample loader as defined in claim 3, wherein said closure member further comprises a spring energized polymeric sealing member within said closure member for forming a substantially gas-tight seal about said boat retrieval rod.

5. The sample loader as defined in claim 4, wherein said closure member further comprises an insulating seal disc having an aperture therein for said boat retrieval rod, said insulating seal disc closing the end of the aperture in said furnace seal member remote from said combustion furnace.

6. A sample loader as set forth in claim 5, wherein said reversible means for moving said furnace seal member comprises a pair of pneumatic cylinders, said pneumatic cylinders being connected between said end plate of said frame member and said furnace seal member.

7. A sample loader as set forth in claim 2, wherein said first end plate for said frame member further includes means for aligning said first end plate, and said frame member further including at least one latch member.

8. A sample loader as set forth in claim 2, wherein said first end plate of said frame member has a circumferential groove about said aperture therein for receiving an elastic sealing member.

9. Sample loader for a horizontal analytical combustion furnace comprising:
  a first frame for attachment to a horizontal combustion furnace comprising a first end plate having an aperture therein;
  a second end plate spaced from said first end plate;
  at least one guide rod extending between said first and second end plates;
  a first carriage movably supported on said guide rod, said carriage comprising a furnace sealing member having an aperture therein and an end member joined together by at least one side member;
  a closure member for said aperture in said furnace sealing member;
  reversible means for moving said furnace sealing member into a sealing position and for moving said seal member away form said sealing position;
  a rotary actuator member;
  a support member for said rotary actuator member movably mounted on said guide rod;
  a boat retrieval rod operatively connected to said rotary actuator and extending through said closure member into said furnace seal member, said boat retrieval rod having a hook on the end thereof remote from said rotary actuator, said rotary actuator reversibly moving said hook on said boat retrieval rod from an inoperative to an operative position; and
  a motor mounted on said first carriage for reversibly moving said support member for said rotary actuator.

10. A sample loader as set forth in claim 9, wherein said closure member comprises:
  a bearing for movably closing a combustion furnace side of said aperture in said furnace seal member around said boat retrieval rod.

11. A sample loader as set forth in claim 10, wherein said closure member comprises a spring energize polymeric sealing member within said closure member for forming a substantially gas tight seal about said boat retrieval rod.

12. A sample loader as set forth in claim 11, wherein said closure member further includes an insulating sealing disk having an aperture therein through which said boat retrieval rod can move.

13. A sample loader as set forth in claim 12, wherein said reversible means for moving said furnace sealing member comprises at least one pneumatic cylinder, said at least one pneumatic cylinder being connected between said end plate of said frame member and said furnace sealing member.

14. A sample loader as set forth in claim 9, wherein said first end plate for said frame member further includes means for aligning said end plate with said gas purging module on said combustion furnace and at least one latch member on said first end plate of said frame member for cooperating with at least one latch member on said gas purging module for releasably fastening said first end plate and said gas purging station to her.

15. A sample loader as defined in claim 14, wherein said first end plate of said frame member has a circumferential groove about said aperture therein for receiving an elastic sealing member and said gas purging module has a circumferential groove about said aperture for receiving an elastic sealing member.

16. A sample loader as set forth in claim 9, wherein said motor for moving said support member for said rotary actuator includes:
  an electric motor mounted at one end of said carriage;
  a driving gear connected to the output shaft of said motor;
  a substantially U-shaped supporting member adjustably attached to said end member of said first carriage;
  a driver gear rotatively mounted between the ends of said U-shaped supporting member;
  a belt operably coupled to said driving and driver gears; and
  a clamp member on said rotating actuator support for griping the ends of said belt and operatively connecting said belt to said rotating actuator support whereby the movement of said belt will cause said rotary actuator support to move.

17. A sample loader as set forth in claim 16 including:
  a first vertical guide rail mounted in one side of said second carriage member;
  a first actuator member movably supported on said first vertical guide rail, said actuator member comprising a pneumatic cylinder having an extendable rod member for pushing combustion boats from said hotel member;
  a second vertical guide rail mounted on the other side of said first carriage member opposite said first vertical guide rail; and
  an elevator movably mounted on said second vertical guide rail for receiving combustion boats from said hotel member and for delivering said combustion boats to a location where said combustion boat can be pushed.

18. A sample loader as set forth in claim 9 including a second frame for supporting said first frame, said second frame comprising an upper horizontal plate vertically separated from a lower horizontal plate by a plurality of vertical column members; and
  a plurality of spaced vertical leveling screws on said second frame for raising and lowering the height of said second frame and for leveling said second frame.

19. A sample loader as set forth in claim 18 wherein said elevator comprises a carriage movably mounted on said vertical guide rail;
  a substantially rectangular box pivotably carried on said spaced supporting arms; and
  a pneumatic cylinder operatively connected between the bottom of said box and said carriage for causing said box to pivot.

20. A sample loader as set forth in claim 9 including a guide rail mounted on said lower horizontal plate, said guide rail extending orthogonally to said combustion tube when said automatic sample loader is attached to an analytical combustion furnace;
- a second carriage movably mounted on said guide rail;
- a hotel member removably mounted on said second carriage said hotel member comprising a frame having a top and a bottom member vertically spaced by attached end members with a plurality of vertically spaced horizontal plates connected at each end to said end members for carrying a plurality of combustion boats; and
- a motor means for moving said second carriage member relative to said combustion tube.

21. A automatic sample loader as defined in claim 20 and further including a shoot depending below an aperture in said upper horizontal plate of said second frame, for receiving a spent combustion boat from aid elevator; and a collection reception on said lower horizontal plate of said second frame for receiving spent combustion boats from said shoot.

* * * * *

UNITED STATES PATENT AND TRADEMARK OFFICE
CERTIFICATE OF CORRECTION

PATENT NO. : 5,314,662
DATED : May 24, 1994
INVENTOR(S) : Hemzy et al.

It is certified that error appears in the above-indentified patent and that said Letters Patent is hereby corrected as shown below:

Col. 2, line 25, insert --in-- after "shown".

Col. 2, line 62, "elevation" should be --elevational--.

Col. 3, line 13, "elevation" should be --elevational--.

Col. 3, line 25, "Boat hotel 52" should be --Boat hotel 56--.

Col. 3, line 37, "shoot" should be --chute--.

Col. 3, line 38, "elevator 54" should be --elevator 64--.

Col. 3, line 39, "launch assembly 68" should be --launch assembly 69--.

Col. 3, lines 40-41, "analytical furnace" should be --analyzer/furnace--.

Col. 4, line 7, "cylinder 117" should be --cylindrical post 107--.

Col. 4, line 11, "vertical supports 112 and 114" should be --vertical supports 114 and 116--.

Col. 4, line 19, "assembly 68" should be --assembly 69--.

Col. 4, line 20, "assembly 68" should be --assembly 69--.

Col. 4, line 25, after "end member 124" insert -- (FIG. 1)--.

UNITED STATES PATENT AND TRADEMARK OFFICE
CERTIFICATE OF CORRECTION

PATENT NO. : 5,314,662
DATED : May 24, 1994
INVENTOR(S) : Hemzy et al.

It is certified that error appears in the above-indentified patent and that said Letters Patent is hereby corrected as shown below:

Col. 4, line 35, "juxtapositions" should be --juxtapositioned--.

Col. 4, line 49, insert --A-- before "DC motor".

Col. 5, line 10, "side walls" should be --sidewalls--.

Col. 5, line 13, "side walls" should be --sidewalls--.

Col. 5, line 22, "Snap connector" should be --Snap-connector--.

Col. 5, line 37, "(FIG. 7)" should be --(FIG. 3)--.

Col. 5, line 53, "backface 209" should be --backface 211--.

Col. 6, line 31, delete "(FIG. 10)".

Col. 6, line 39, "bottom shelf 78" should be --bottom shelf 68--.

Col. 6, line 44, "axle 251" should be --axle 255--.

Col. 6, line 51, "257" should be --251--.

Col. 6, lines 51-52, delete "tilting rod 250 when the hotel is moved between the rest and the dump positions".

UNITED STATES PATENT AND TRADEMARK OFFICE
CERTIFICATE OF CORRECTION

PATENT NO. : 5,314,662
DATED : May 24, 1994
INVENTOR(S) : Hemzy et al.

Page 3 of 7

It is certified that error appears in the above-indentified patent and that said Letters Patent is hereby corrected as shown below:

Col. 6, line 54, "posit" should be --position (Fig. 9)--.

Col. 6, line 65, "a" should be --and--.

Col. 6, line 66, "shoot" should be --chute--, both occurrences.

Col. 6, line 67, "shoot" should be --chute--.

Col. 7, line 1, "shoot" should be --chute--.

Col. 7, line 9, "assembly 68" should be --assembly 69--.

Col. 7, line 15, insert --76-- after "retrieval rod".

Col. 7, line 46, delete "moves".

Col. 7, line 47, "(FIG. 3)" should be --(FIG. 13)--.

Col. 7, line 53, "(FIG. 14)" should be --(FIGS. 4 and 14)--.

Col. 7, line 58, insert --$A_2$-- after "axis".

Col. 7, line 60, "A1" should be --$A_1$ (FIG. 15)--.

Col. 7, line 66, "400" should be --317--, both occurrences.

Col. 7, line 67, "400" should be --317--.

UNITED STATES PATENT AND TRADEMARK OFFICE
CERTIFICATE OF CORRECTION

PATENT NO. : 5,314,662
DATED : May 24, 1994
INVENTOR(S) : Hemzy et al.

It is certified that error appears in the above-indentified patent and that said Letters Patent is hereby corrected as shown below:

Col. 8, line 1, "400" should be --317--.

Col. 8, line 5, "401" should be --325--.

Col. 8, line 6, "403" should be --327--.

Col. 8, line 13, "Teflon" should be --TEFLON--.

Col. 8, line 13, "bushing 340" should be --bushing or disc 340--.

Col. 8, line 15, "teflon" should be --TEFLON--.

Col. 8, line 18, "teflon" should be --TEFLON--.

Col. 8, line 28, "teflon" should be --TEFLON--.

Col. 8, line 29, "disk" should be --disc--.

Col. 8, line 30, "Disc 340" should be --Bushing or disc 340--.

Col. 8, line 35 "0-ring" should be --O-ring--, both occurrences.

Col. 8, line 52, delete "(FIG. 19)".

UNITED STATES PATENT AND TRADEMARK OFFICE
CERTIFICATE OF CORRECTION

PATENT NO. : 5,314,662
DATED : May 24, 1994
INVENTOR(S) : Hemzy et al.

Page 5 of 7

It is certified that error appears in the above-indentified patent and that said Letters Patent is hereby corrected as shown below:

Col. 8, line 63, "0-ring" should be --O-ring--.

Col. 9, line 2, after "90" insert --(FIG. 7)--.

Col. 9, line 7, after "418" insert --(FIG. 4)--.

Col. 9, line 32, after "464" insert --(FIG. 1)--.

Col. 9, line 56, after "452" insert --(FIG. 3)--.

Col. 9, line 61, after "194" insert --(FIG. 3)--.

Col. 10, line 6, "458" should be --471--.

Col. 10, line 7, "458" should be --471--.

Col. 10, line 8, "solenoid" should be --solenoids--.

Col. 11, line 10, "400" should be --317--.

Col. 11, line 18, "400" should be --317--.

Col. 11, line 40, "400" should be --317--.

Col. 11, line 47, "400" should be --317--.

Col. 11, line 59, "400" should be --317--.

Col. 12, line 27, "shoot" should be --chute--.

UNITED STATES PATENT AND TRADEMARK OFFICE
CERTIFICATE OF CORRECTION

PATENT NO. : 5,314,662
DATED : May 24, 1994
INVENTOR(S) : Hemzy et al.

Page 6 of 7

It is certified that error appears in the above-indentified patent and that said Letters Patent is hereby corrected as shown below:

Col. 12, line 49, "400" should be --317--.

Col. 14, line 13, claim 1, "ember" should be --member--.

Col. 14, line 44, claim 2, delete "moving said" and "said", second occurrence.

Col. 15, line 7, claim 6, "claim 5" should be --claim 3--.

Col. 16, line 11, claim 14, "to her" should be --together--.

Col. 18, line 6, claim 21, "shoot" should be --chute--.

Figure 7:
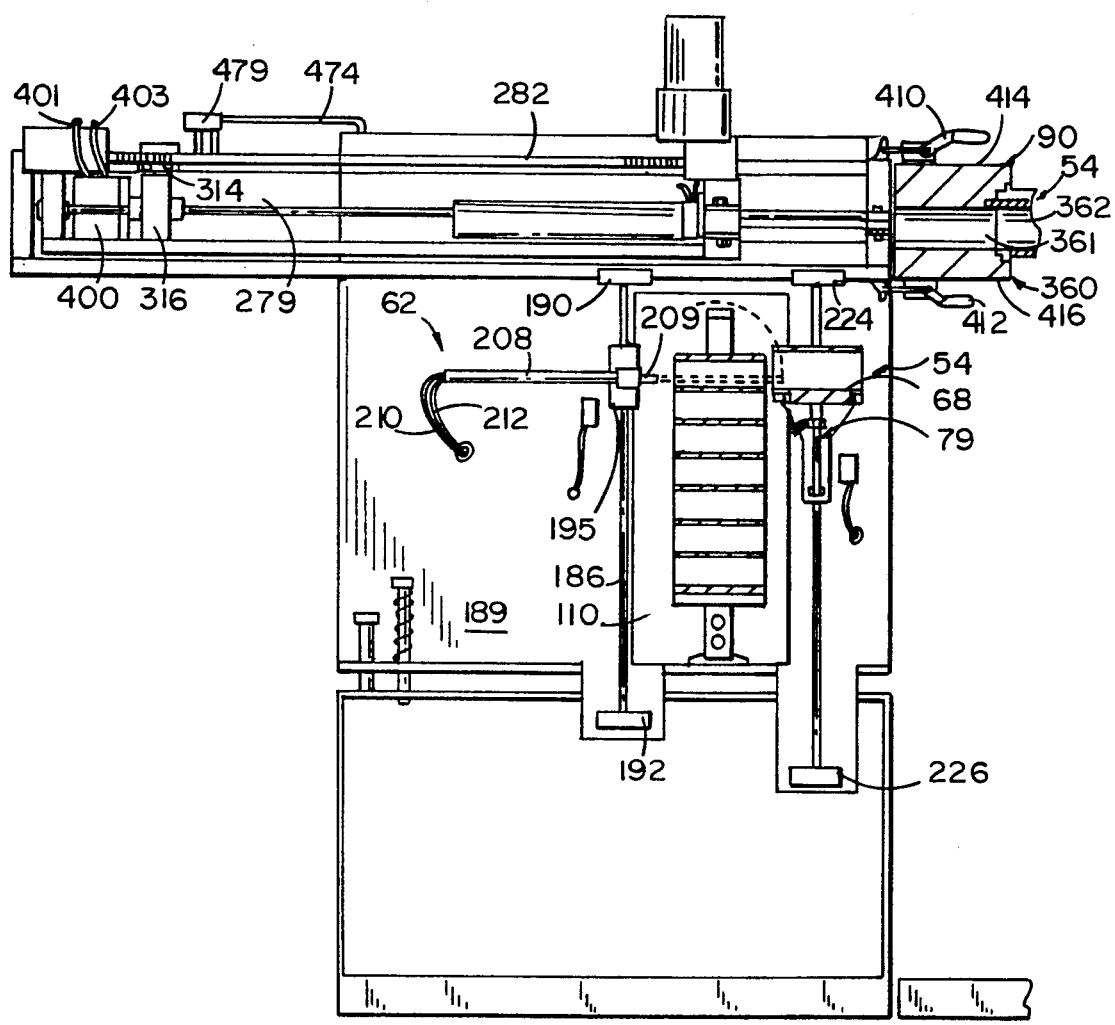
FIG. 7 is a front elevational view of the autoloader with the boat hotel, boat elevator box, purge chamber, and furnace chamber cut away.

In Fig. 1, element "68" should be --69--, element "463" should be --468--, and element "367" should be --361--;

In Fig. 6, element "236" should be --237--;

In Fig. 7, element "400" should be --317--; and

UNITED STATES PATENT AND TRADEMARK OFFICE
CERTIFICATE OF CORRECTION

PATENT NO. : 5,314,662
DATED : May 24, 1994
INVENTOR(S) : Hemzy et al.

It is certified that error appears in the above-indentified patent and that said Letters Patent is hereby corrected as shown below:

In Fig. 19, element "458" identifying the solenoid interface, should be --471--.

Signed and Sealed this

Eighth Day of July, 1997

*Attest:*

*Attesting Officer*

BRUCE LEHMAN

Commissioner of Patents and Trademarks